United States Patent [19]

Ling et al.

[11] Patent Number: 5,733,270

[45] Date of Patent: Mar. 31, 1998

[54] METHOD AND DEVICE FOR PRECISE RELEASE OF AN ANTIMICROBIAL AGENT

[75] Inventors: Michael T. K. Ling, Vernon Hills; Lecon Woo, Libertyville; Ying-Cheng Lo, Green Oaks, all of Ill.; Patrick Balteau, Saint-Denis; F. Peluso, Heverlee, both of Belgium

[73] Assignee: Baxter International Inc., Deerfield, Ill.

[21] Appl. No.: 474,839

[22] Filed: Jun. 7, 1995

[51] Int. Cl.⁶ ....................................... A61M 1/00
[52] U.S. Cl. ................ 604/32.6; 604/85; 604/203; 604/905
[58] Field of Search ..................... 604/82, 890.1, 604/4, 7, 19, 27, 56, 57, 84, 92, 257, 262, 265, 403, 408, 85, 326, 283, 905

[56] References Cited

U.S. PATENT DOCUMENTS

| | | |
|---|---|---|
| 4,249,562 | 2/1981 | King, Sr. . |
| 4,381,380 | 4/1983 | LaVeen et al. . |
| 4,624,847 | 11/1986 | Ayer et al. . |
| 4,968,439 | 11/1990 | LaVeen et al. . |
| 5,004,614 | 4/1991 | Staniforth et al. . |
| 5,026,359 | 6/1991 | Burroughs . |
| 5,070,889 | 12/1991 | LaVeen et al. . |
| 5,071,648 | 12/1991 | Rosenblatt . |
| 5,156,164 | 10/1992 | LaVeen et al. . |
| 5,344,411 | 9/1994 | Domb et al. . |

FOREIGN PATENT DOCUMENTS

| | | |
|---|---|---|
| 0126650 | 11/1984 | European Pat. Off. . |
| 61-171403 | 8/1986 | Japan . |
| 1 437 835 | 6/1976 | United Kingdom . |
| WO 9215286 | 9/1992 | WIPO . |

OTHER PUBLICATIONS

Jensen et al, *In-Vitro Efficacy of a Central Venous Catheter Complexed with Iodine to Prevent Bacterial Colonization*, J. Antimicrob. Chemother., vol. 30, pp. 135-139 (1992).

Kristinsson et al, *Antimicrobial Activity of Polymers Coated with Iodine-Complexed Polyvinylpyrrolidone*, J. Biomater. Appl., vol. 5, pp. 173-184 (1991).

LaVeen et al, *The Mythology of Povidone-Iodine and the Development of Self-Sterilizing Plastics*, Surg. Gynecol. Obstet., vol. 176, pp. 183-190 (1993).

Primary Examiner—Michael Powell Buiz
Assistant Examiner—N. Kent Gring
Attorney, Agent, or Firm—Thomas S. Borecki; Charles R. Mattenson; Robert M. Barrett

[57] ABSTRACT

An improved system and method for providing sterile connections. To this end, a device is provided comprising a body, a chamber defined, at least in part, by a portion of the body, the chamber including an interior having a solid sterilizing agent that can sublimate at ambient conditions, and a member that defines, in part, the chamber and is so constructed and arranged to allow the solid sterilizing agent to release in a rate controlled manner through the member.

14 Claims, 7 Drawing Sheets

METHOD AND DEVICE FOR PRECISE RELEASE OF AN ANTIMICROBIAL AGENT

BACKGROUND OF THE INVENTION

The present invention relates generally to methods and devices that utilize or include disinfectants. More specifically, the present invention relates to connectors and methods of making sterile connections.

In a variety of industries, it may be necessary to provide a device that includes at least one surface that has been sterilized. For example, in the medical industry, it is important to insure that products that are introduced into the body and provide a pathway into the body do not cause an infection due to microbials, such as bacteria. One means by which such infections can be caused is due to connections that create a fluid flow path between an access site in the body and a medical product to be infused into the body.

For example, it is, of course, generally known to provide fluid delivery to a patient for a variety of purposes, such as the delivery of a medicament, provide dialysis, and the like. Such fluid delivery necessitates in many instances, the creation of sterile fluid paths. Some such medical procedures require that the sterile fluid paths be disconnected and reconnected.

For example, it is known to use a cannula or needle to inject into a patient a solution through the use of a length of tubing which is further connected to a container housing a solution. Often, an adapter or other connector is provided for enabling fluid communication between the container and the patient through the tubing. For example, a connector may be provided at a port on a container to connect an end of the length of tubing to the container.

In the medical industry, it is also well known to provide solutions to a patient, such as for peritoneal dialysis. In peritoneal dialysis, a dialysis solution is introduced into the peritoneal cavity utilizing a catheter. After a sufficient period of time, an exchange of solutes between the dialysate and the blood is achieved. Metabolic waste removal is achieved by providing a suitable osmotic gradient. The dialysis solution is then simply drained from the body cavity through the catheter.

This procedure is generally repeated three or four times daily for such a patient. Therefore, repeated connections and disconnections are required to be made from the system. Additionally, during the procedure, the patient may be interrupted due to daily activities, such as answering the door or telephone. This may require that the patient disconnect and reconnect the system during a procedure.

At least three issues arise with respect to the disconnection and reconnection of a sterile flow path, such as that used for peritoneal dialysis. One requirement is that the system must provide a quick and simple method for disconnection from the system. It is also required that a sterile, contaminant-free, environment be maintained after disconnection. Further, such a system must provide means for a simple reconnection to the system.

If the system is so complicated that it requires dismantling the entire set-up, a patient generally will not permit the interruption and will continue receiving the solution ignoring the interruption, e.g. not answering the telephone or door. On the other hand, if the disconnection and/or reconnection cannot be performed without contaminating the system, contaminated system components must be replaced. In the alternative, the contaminated components of the system must be sterilized before reuse of the system. Again, therefore, a patient will ignore the interruption and will continue with the administration of the solution from the system.

However, despite the patient's desire, at times, interruptions, such as emergencies, require disconnection from the system. Therefore, systems must be provided that allow for the disconnection or reconnection of systems without contamination of the components of the system.

In other areas of the medical industry, the industry continues to strive to reduce the incidence of bacteria infection caused by bacteria contamination due to medical devices or procedures. This is particularly true with respect to medical apparatus that cannot normally be sterilized and autoclaved or which are used in bacteria containing environments.

For example, sutures, catheters, surgical tape, tubings, sponges, gloves, pads, surgical covers, dialysis connectors, and certain medical instruments cannot be autoclaved to insure sterility. They often must be used in areas where pathogenic bacteria are encountered. Accordingly, for such medical apparatus, the art has long sought means and methods for rendering those medical apparatus antibacterial and, hopefully, antimicrobial.

The general approach in the art has been that of coating a medical apparatus, or a surface thereof, with a bactericide. However, since most bactericides are partially water soluble, or at least require sufficient solubilization for effective antibacterial action, simple coatings of bactericides have been proven unreliable. For this reason, the art has sought to incorporate the bactericides into the medical apparatus or at least provide a stabilized coating thereon.

For example, with the increased use of polymeric materials for the construction of medical apparatus, utilizing an antimicrobial polymer has become even more desirable. The art, therefore, has sought various combinations of plastics and antibacterial agents. The antibacterial agent could be fixedly attached to or incorporated in the plastic, so that the combination thereof can be used for the manufacture of these plastic medical apparatus.

This relatively recent effort in the art has taken a myriad of different approaches. For example, U.S. Pat. No. 3,401,005, in an attempt to create a product that functions satisfactorily, applies a composition of polyvinylpyrrolidone and iodine to cotton gauze. When dried, the coated material would have a germicidal characteristic. In a similar effort, a complexed composition of polyvinylpyrolidone and iodine was placed in absorbable, gelatin foams to produce surgical sponges. In U.S. Pat. No. 3,401,005, the complexed composition was found to release iodine under use conditions.

Solid polyvinylpyrrolidone complexed with iodine is disclosed in U.S. Pat. No. 3,898,326 as useful as a disinfectant material. U.S. Pat. No. 4,017,407 extends this complexed composition to include detergents.

U.S. Pat. No. 4,381,380 relates to a polymeric bactericidal composition for use in antibacterial applications. The composition of U.S. Pat. No. 4,381,380 contains a plastic, sparingly cross-linked polyurethane having —O—(CO)—NH— urethane linkages and iodine complexed with a sufficient number of the linkages to provide bactericidal properties to the composition. Iodine solutions having concentrations of from 1% to 15% were utilized for complexing the iodine with the urethane linkages.

Utilizing a plastic completely complexed with iodine as a potential self-sterilizing material has disadvantages. Among other factors, the concentration of the iodine in the solution and the solvent of the iodine solution limits the amount of iodine complexed with the polyurethane. Further, the rate of release of iodine from plastics complexed with iodine depends upon the affinity the plastic has for iodine. As a result, these complexed plastics often do not provide an effective delivery of iodine into the atmosphere or a liquid for sufficient antimicrobial treatment.

U.S. patent application Ser. No. 08/366,336 filed on Dec. 28, 1994 provides an antimicrobial material including a plastic material and a molecular halogen entrapped within the plastic material. The molecular halogen is primarily absorbed into the plastic material and only some, if any, is complexed with the plastic material.

In providing such products, a variety of factors must also be considered in addition to providing sterility. Many of the products to be treated require that the antimicrobial function be provided over a prolonged period of time, e.g., several months.

Additionally, because the microbial burdens encountered over time at various clinical and home settings can be very diverse, encompassing nearly all strains of bacterial, fungal, and viral families, the antimicrobial agent must have a broad spectrum in its ability to neutralize these infectious agents. Preferably, little or no resistance should build up through the mutation of the microbial agents against the disinfectant.

Still another requirement for the antimicrobial agent is relatively low toxicity to human tissues over long term contact. This requirement stems from the consideration for the patient and medical personnel safety.

SUMMARY OF THE INVENTION

The present invention provides an improved system and method for providing sterile connections.

To this end, the present invention provides a device comprising a body, a chamber defined, at least in part, by a portion of the body, the chamber including an interior having a solid sterilizing agent that can sublimate at ambient conditions, and a member that defines, in part, the chamber and is so constructed and arranged to allow the solid sterilizing agent to sublimate in a rate controlled manner through the member.

In an embodiment, the member is porous.

In an embodiment, the solid sterilizing agent is iodine.

In an embodiment, the device includes means for coupling the device to another component.

In an embodiment, the device includes a fluid flow path through the device, the solid sterilizing agent contacting at least portions of the fluid flow path after it sublimates through the member for at least portions of the time.

In an embodiment, the device includes means for coupling the device to another component that includes a second fluid flow path and causing the fluid flow path and second fluid flow path to be in fluid communication.

In another embodiment of the invention, a method for disinfecting an area is provided comprising the steps of providing a product having an area, housing a solid disinfectant that sublimates at ambient temperatures in a container that includes a member that is in juxtaposition to the area, and allowing the solid disinfectant to sublimate through the member into the area in a rate controlled manner.

In an embodiment of the method, the solid disinfectant is iodine.

In an embodiment of the method, the product is a connector used in a medical procedure. In a further embodiment of the method, the medical procedure is dialysis.

In an embodiment of the method, the member includes pores.

In still another embodiment, the present invention provides a medical device comprising a body including a fluid flow pathway therethrough, a chamber member defining an interior, portions of the body defining the chamber, the chamber including a controlled release member. A solid sterilizing compound that sublimates at ambient conditions is located within the chamber. And the controlled release member is so constructed and arranged to allow at least some of the sublimated solid sterilizing compound to pass through the controlled release member and contact at least portions of the fluid flow pathway.

In yet another embodiment of the present invention, a system is provided for coupling two flow pathways together comprising a first member including a first fluid flow pathway, a second member including a second fluid flow pathway therethrough. The first member includes a chamber defining an interior including a controlled release member. A solid sterilizing compound is located within the chamber and sublimates at ambient conditions. The controlled release member is so constructed and arranged to allow at least some of the solid sterilizing compound to sublimate and pass through the controlled release member and contact at least portions of the fluid flow pathway. Means for removably coupling the first and second members together are provided so as to allow the first and second fluid flow pathways to be in fluid communication.

Further, in another embodiment of the present invention, a method for performing peritoneal dialysis is provided comprising the steps of implanting in the patient a catheter that includes at an end thereof a device comprising a body member including a fluid flow pathway therethrough, a chamber member defining an interior, the chamber including a controlled release member, a solid sterilizing compound is located within the chamber that sublimates at ambient conditions. The controlled release member is so constructed and arranged to allow at least some of the solid sterilizing compound to sublimate and pass through the controlled release member and contact at least portions of the fluid flow pathway.

An advantage of the present invention is to provide an improved method for providing a sterile structure.

An additional advantage of the present invention is to provide an improved disinfectant system.

Still further, an advantage of the present invention is to provide an improved system that can be used in medical devices.

Moreover, an advantage of the present invention is to provide a sterile connection system for use in the medical industry.

Further, an advantage of the present invention is to provide improved CAPD connectors.

Additionally, an advantage of the present invention is to provide a system for sterilizing devices solutions that is self-regulating in the amount of disinfectant that is released.

Furthermore, the present invention provides a method and apparatus for providing antimicrobial action in an extremely compact form and small physical size providing patient convenience, mobility, and ease of product manufacturing.

Another advantage of the present invention is that it provides a system for providing antimicrobial action that can be used for long term antimicrobial action, e.g., several months.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a system and method for sterilizing products, such as medical devices, and more specifically, connectors used in or with medical devices. Although the present invention, in the embodiment described below, is used for medical devices and specifically connectors for use in continuous ambulatory peritoneal dialysis (CAPD), it should be appreciated that the present invention can be used for a variety of other devices in the medical industry and even outside the medical industry wherein antimicrobial agents are necessary.

To this end, the present invention provides a method and system for the controlled release of an antimicrobial agent. Pursuant to the present invention, an antimicrobial agent is provided having a significant vapor pressure at room temperature. The antimicrobial agent is used in a substantially pure, uncomplexed form. Halogens, halogen compounds, and especially molecular iodine are especially useful for this purpose.

As set forth in detail below, the antimicrobial agent is enclosed in a space where at least one of the surfaces is essentially impervious and unreactive to the agent. However, at least one rate controlling member for delivery of the antimicrobial agent in substantially its vapor form is provided. To provide a rate controlling member at least one wall, or surface is provided that allows for the diffusion of the antimicrobial agent therethrough.

In an embodiment, the surface is of a porous nature wherein the density of the structure and the pores control the delivery of the antimicrobial agent. However, the device can also be dense and pore free and control of the delivery is thereby through molecular diffusion of the antimicrobial agent through the thickness of the device.

The present invention provides many advantages for a system and method for delivering antimicrobial agents. First, the rate of delivery of the antimicrobial agent can be precisely controlled by the pore structures, size of the area for permeation, the height/length of the member and the selection of material in the case of molecular diffusion.

Because the antimicrobial agent is in substantially its pure form, the total amount of antimicrobial agent that can be delivered is significantly greater than that for a complexed agent. In this regard, in a complexed agent only a minority of the complexed mass constitutes the active agent. Because, in the present invention, the antimicrobial agent is provided in substantially its pure form, this greater capacity allows the antimicrobial agent to be maintained and available over a much longer period of time.

Additionally, the present invention provides for the separation of the storage function and release regulating function for the antimicrobial agent. This allows significant freedoms in the design and assembly of the device.

Still further, the pure form of the active agent reduces the bulk and size of the container necessary for housing the agent. This allows one to provide a device that affords greater patient convenience.

Separation of function also allows the release of antimicrobial agent to be directional. In this regard, the release of antimicrobial agent is controlled by the orientation and location of the delivery surface with respect to the volume where the antimicrobial agents are required.

As noted above, the present invention, in an embodiment, will be described with respect to use in a CAPD connection system; again, however, the application is not so limited. U.S. patent application Ser. No. 08/295,112, filed on Aug. 24, 1994 and entitled: "Transfer Set Connector With Permanent, Integral Cam Opening Closure and a Method of Using the Same" describes a connection device for a CAPD system. That disclosure is hereby incorporated by reference.

Generally, the device of that application provides a connector assembly and a method of connecting a pair of connectors to provide fluid communication between a first length of tubing and a second length of tubing. The connector assembly incorporates a hinged closure providing sealed connection and disconnection of the assembly upon connection of the connectors. In an embodiment, the connector assembly comprises a male component connected to a first length of tubing and a female component connected to a second length of tubing. The female component selectively mates with the male component providing communication between the first length of tubing and the second length of tubing. The female component comprises a hinged closure providing selected access to an orifice of the female component. Preferably, the hinged closure of the connector assembly includes a spring to maintain a seal of the hinged closure.

Figure 1:
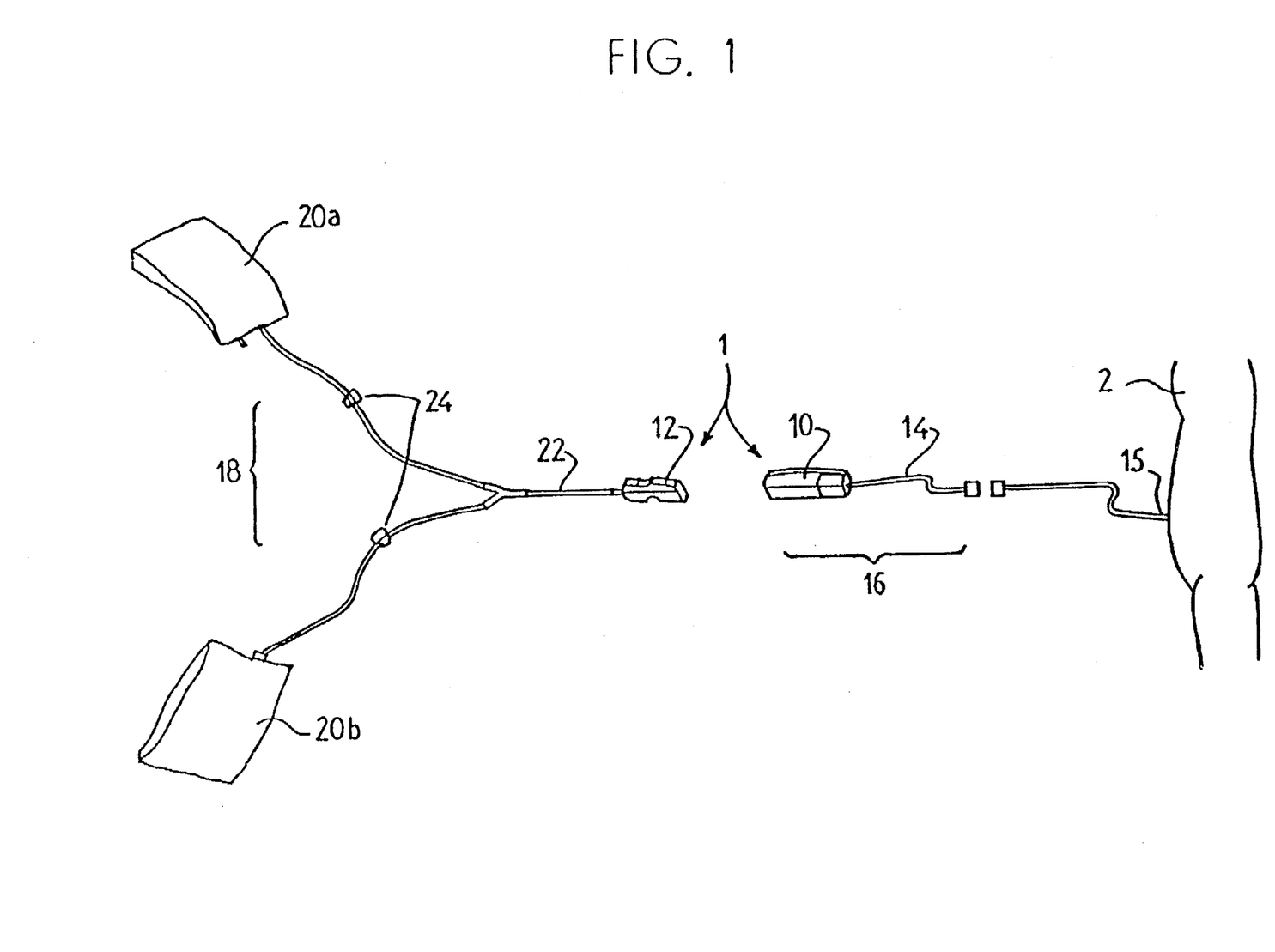
FIG. 1 illustrates an environmental view of a connector of the present invention in its disconnected state between a fluid source and a patient.

Referring now to the drawings, FIG. 1 illustrates an environmental view of a system employing the connector 10 of the present invention. The connector 10 is part of a connection system that is generally illustrated at 1 and includes the connector 10 that is a female component and a male component 12. As illustrated in FIG. 1, in a preferred embodiment of the present invention, the female component 10 is connected to a conduit 14 which is attached via a catheter 15 to a patient 2.

The male component 12, on the other hand, in a preferred embodiment, may be connected to a Y-set generally illustrated at 18. The Y-set 18 includes two containers 20a, 20b. Typically, for peritoneal dialysis, one of the containers, for example, the container 20a, is filled with a dialysate and the other container 20b is empty. The containers 20a and 20b are attached to the male component 12 through a length of conduit 22 to control flow of dialysate as desired. In another embodiment, the male component 12 of the connector 1 may have clamps integrated into its housing.

Figure 2:
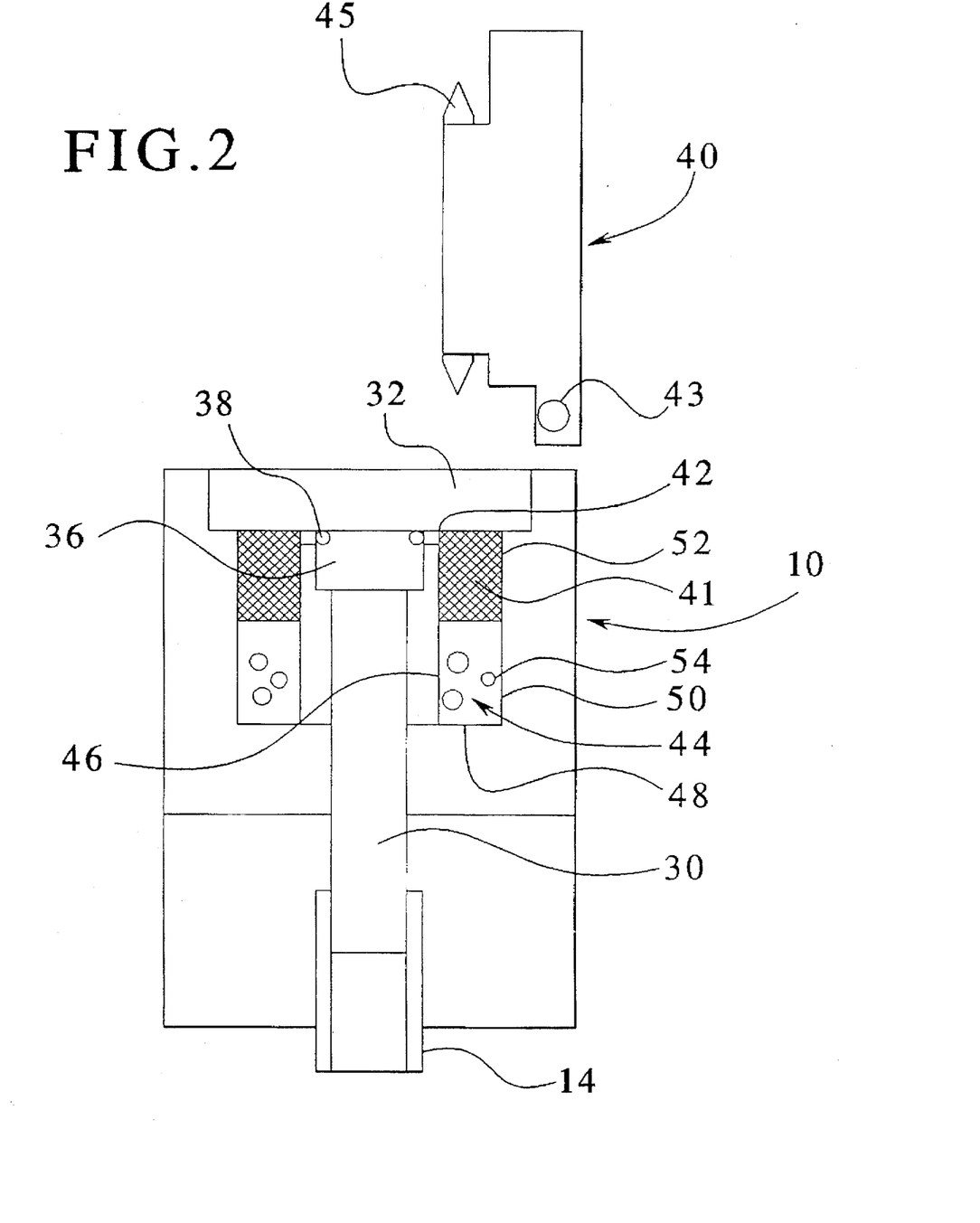
FIG. 2 illustrates a cross-sectional view of an embodiment of the connector of FIG. 1.

Referring now to FIG. 2, the connector 10 is illustrated. In the embodiment illustrated, the connector 10 includes a channel 30 that creates a fluid path from an open well 32 to a tubing 14 that is in fluid communication with the catheter on the patient 2. The channel 30 includes an opening 36 that has a greater diameter than the remaining portions of the channel. The opening 36 is designed to receive a catheter from the second male member 12 of FIG. 1. This will create a fluid flow path from the CAPD fluid source, or an empty CAPD bag, and the patient. Preferably, the opening 36 includes a seal 38 for sealingly receiving the catheter. However, in another embodiment, the seal is provided on the catheter.

As illustrated, the connector 10 includes a cover 40 for covering the open well 32 and opening 36 of the channel 30. As discussed in detail in U.S. patent application Ser. No. 08/295,112, in the embodiment of the connector 10 illustrated in FIGS. 1 and 2, the male component 12 is designed to bias open the cover 40 allowing a connection between the female connector 10 and the male component 12. To this end, the cover can pivot on a metal pin 43 that secures the cover 40 to the remaining portions of the connector 10. Preferably, the cover includes a fluorocarbon lip seal 45.

Pursuant to the present invention, in order to provide a sterile fluid flow path through the channel 30 of the connector 10, the connector includes a rate controlling antimicrobial agent releasing system 41. In a preferred embodiment illustrated, the system 41 circumscribes the opening 36 of the channel member 30. Due to the location of the system 41, antimicrobial agent is released and sterilizes the surfaces of the enclosed well 32 when the cover 40 is closed in addition to the opening 36 and the channel 30.

The rate controlling antimicrobial releasing system 41 includes an internal chamber 44. The internal chamber 44 is defined by wall members 46, 48, 50, and 52. Located within the chamber 44 is a solid antimicrobial agent 54.

In the preferred embodiment illustrated, wall members 46, 48, and 50 are impervious and unreactive to the antimicrobial agent 54. However, the system 41 includes an antimicrobial releasing wall member 52. The antimicrobial releasing wall member 52 allows the antimicrobial agent, which is in a solid form in the chamber 44, to diffuse through the wall. This allows the antimicrobial agent 54 to diffuse across the surface of the wall 52 and open well 32, as well as into parts of the channel 30 including the opening 36 therein.

The diffusion of the antimicrobial agent sterilizes the connection between the female connector 10 and male component 12. In this regard, even though the cover 40 of the connector 10 is closed, the antimicrobial agent will saturate and diffuse across the well 32. Accordingly, when it is time to make a connection between the two devices 10 and 12, the antimicrobial agent will be in place to sterilize the surface of the catheter being inserted into the channel 30 of the connector 10, as well as sterilize and decontaminate any contaminants that may be present during the connection.

Of course, the system 41 can be used on a variety of different connection systems, as well as different medical devices. What is required for the system is the use of a solid disinfectant. As set forth above, the solid disinfectant is preferably a halogen, such as iodine. The disinfectant must be capable of sublimation at ambient conditions. Additionally, the system requires that a member be present that allows for the diffusion of the halogen through the member and thereby provides a rate controlling release of the halogen. In part, the release rate of the antimicrobial agent is a function of its pressure within the chamber as well as the geometry and structure of the member.

A variety of different materials can be utilized for the rate controlling release member of the present invention. In an embodiment, the member is porous. A variety of different porous plastics may be used including thermoplastic polymers, such as polyethylene, polypropylene, PVF, PTEC, nylon, PES, and similar materials.

Figure 3:
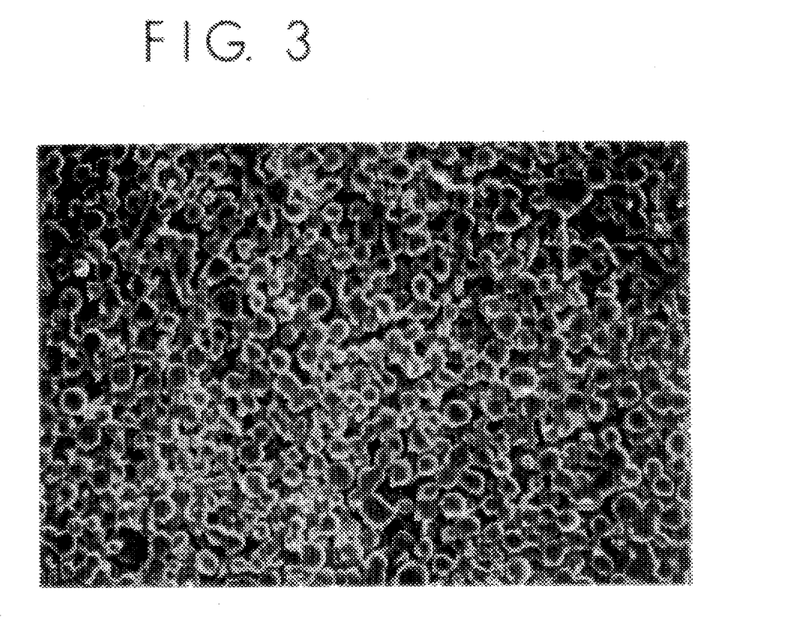
FIG. 3 is a scanning electron micrograph at 200× magnification of microporous material that can be used in the present invention.
Figure 4:
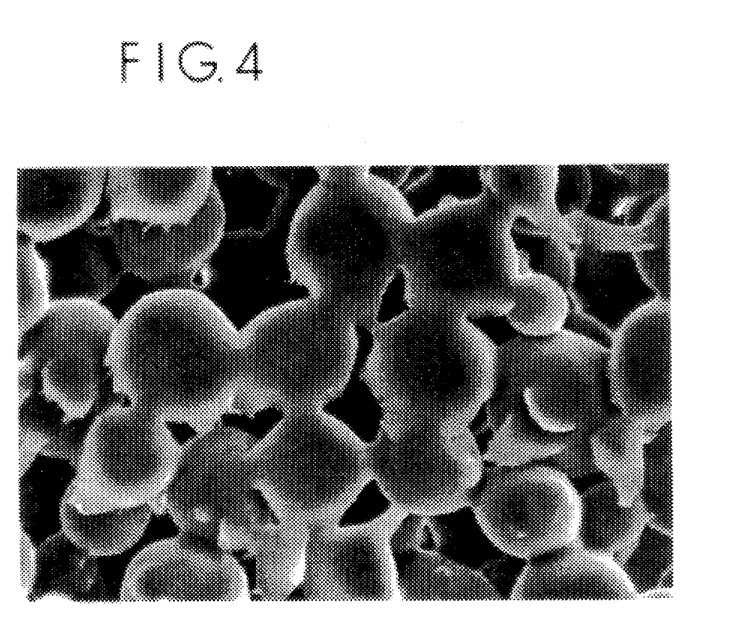
FIG. 4 is a micrograph of the material of FIG. 3 at 1000× magnification.

For example, a porous wall member can be utilized such as that sold by Porex Technologies of Fairburn, Ga. under the tradename Porex®. It has been found that a Porex material constructed from a polymer of ultra high molecular weight polyethylene (UHMWPE) having 5 to 15 micron pores can be satisfactorily utilized in a CAPD connector. The Porex® material is a microporous material with known pore size. Porex® is permeable to vapor, but not aqueous liquids; e.g., it is hydrophobic. It provides a material that is impervious to microorganisms. Additionally, the material allows for a constant rate of delivery of the antimicrobial material. FIGS. 3 and 4 illustrate photomicrographs of the Porex® material. FIG. 3 illustrates the Porex material at 200× magnification. FIG. 4 illustrates the Porex material at 1000× magnification.

For a porous structure, the density and structure of the pores control, at least in part, the delivery of the antimicrobial agent. By selection of the pore structures, size of the area for permeation, length/height and selection of material, the delivery of the antimicrobial agent can be precisely controlled.

However, the rate controlling release member can also be dense and pore-free. The control of delivery of such a member thereby through molecular diffusion of the antimicrobial agent through the thickness of the member. One such material that can be used as the antimicrobial releasing wall is inert polymeric material. By selection of the material and thickness of the wall structure, the rate of delivery of the antimicrobial agent can be precisely controlled.

Materials that it is believed can be used for the antimicrobial releasing member include: sintered polymers, metals, and ceramics; non-wovens, such as Tyvex® (HDPE); microporous membranes; track etched membranes; and dense film structures such as polyesters, thermoplastic elastomers, and low density polyolefins. Preferably, the material is hydrophobic.

By way of example, and not limitation, examples illustrating the present invention will now be set forth.

EXAMPLE NO. 1

Iodine Requirement for Microbial Kill

Saturated iodine water (~300 PPM) was diluted with Dianeal® or Nutrineal™ solution, available from Baxter Healthcare Corporation, to a desired concentration for a microbial kill test. For example, to obtain 100 PPM solution, 1 ml of $I_2$ saturated water was mixed with 2 ml of Dianeal® or Nutrineal™ solution. Because of the strong reaction between iodine and Nutrineal™, and therefore, loss of activity, during the antimicrobial activity determination *Staphylococcus Aureus* is added both before and after the dilution solution to examine the sequence effect.

The following table (Table 1) illustrates the result after one hour of dwell. Since the iodine release rate is not a factor in this example, the dwell time is relatively immaterial. This means that extension of dwell time does not kill more bacteria.

TABLE NO. 1

| Iodine concentration (PPM) or μg/g | Log reduction in one hour | | |
|---|---|---|---|
| | Dianeal® (1.5%) | Nutrineal™ | Complex Carbohydrate Solution |
| Iodine | | | |
| 100[a] | 5.77 | 3.36 | 3.45 |
| 50[a] | — | 2.19 | — |
| 10[a] | 5.77 | 0.91 | 0.32 |
| 1[a] | 0 | 0.24 | 0 |
| 100[b] | 5.32 | 6.23 | 4.95 |
| 50[b] | 5.32 | 2.47 | 1.73 |
| 10[b] | 5.32 | 0.37 | 0.22 |
| 1[b] | — | 0.19 | — |
| Betadine® | | | |
| 100[a] | 5.77 | 0.82 | 0.44 |
| 50[a] | — | 0.67 | — |
| 10[a] | 5.77 | 0.19 | 0.14 |
| 1[a] | 0 | 0.12 | 0.07 |

[a]S.A. bacteria is added to the iodine disinfectant dialysate solution.
[b]S.A.. bacteria is added to the dialysate solution first and added the iodine disinfectant concentrate.

EXAMPLE NO. 2

Determination of Iodine Release Rate into Air and H$_2$O Environment

Figure 5:
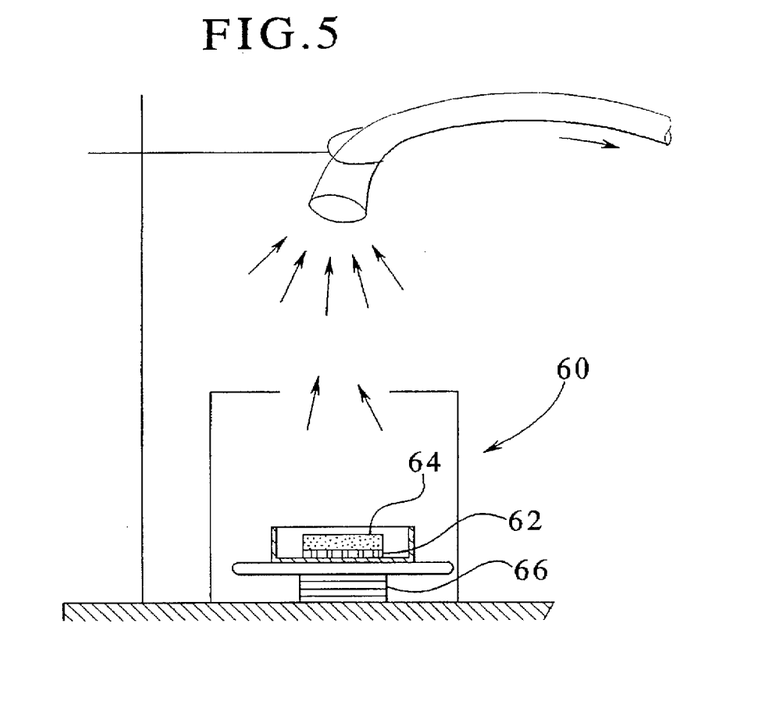
FIG. 5 illustrates schematically a device used in Example No. 2.

A systematic setup 60 to measure the iodine release rate by permeation throughout the UHMWPE microporous material into the air environment is shown in FIG. 5. Roughly 1×1 in$^2$ of iodine solid 62 was prepared from the iodine powder by compression molding. A piece of UHMWPE microporous sheeting 64, POREX®, was then cut and trimmed to size to cover the iodine sublimation surface 62. The POREX® 64 was placed on the top of the iodine sublimation surface 62 which was placed on a microbalance 66. The release rate measurement was determined by the micro-balance 66. A house vacuum 68 was placed roughly 24 inches above the testing article to remove the volatile iodine gas.

Figure 6:
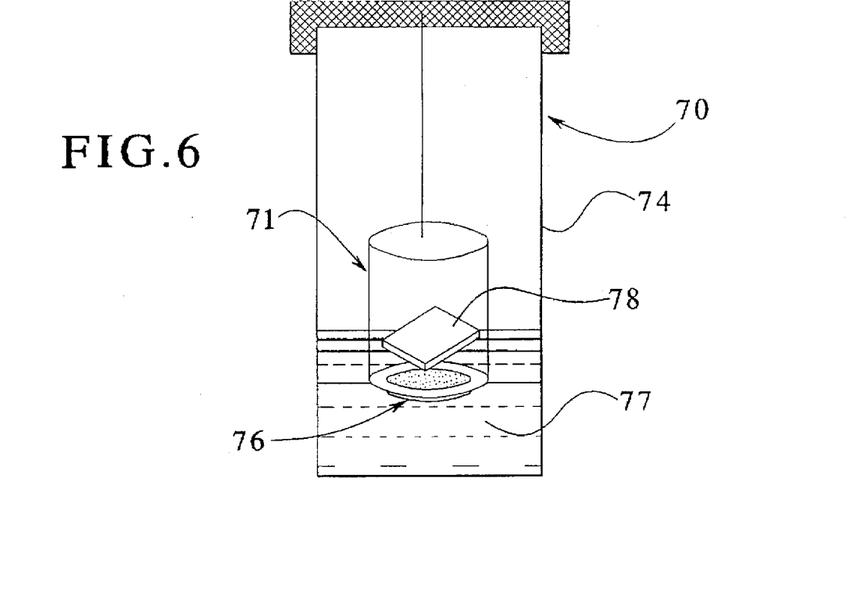
FIG. 6 illustrates schematically another device used in Example No. 2.

FIG. 6 illustrates a setup 70 for release into water 77. A container 71 including the POREX® wall 76 (similar to wall 64 of FIG. 5) was located in a glass vial 74. The amount of iodine 78 released into the water 77 was measured by UV spectrophotometer at ABS 460 nm.

Figure 7:
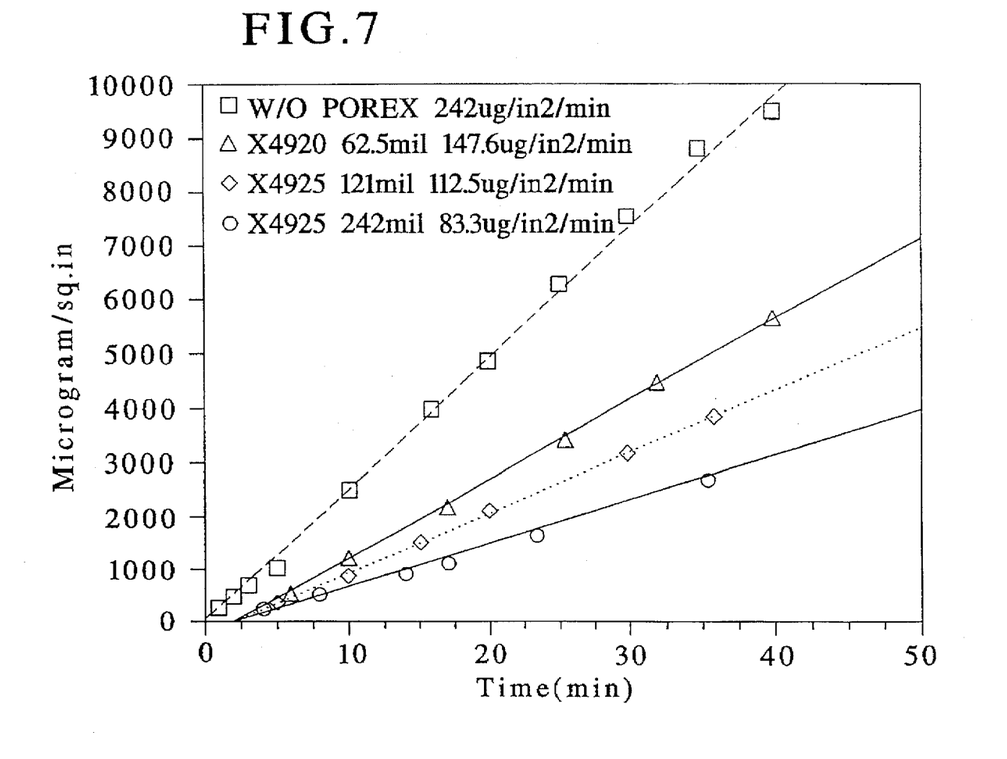
FIG. 7 illustrates graphically results of Example No. 2 setting forth iodine release versus thickness.
Figure 8:
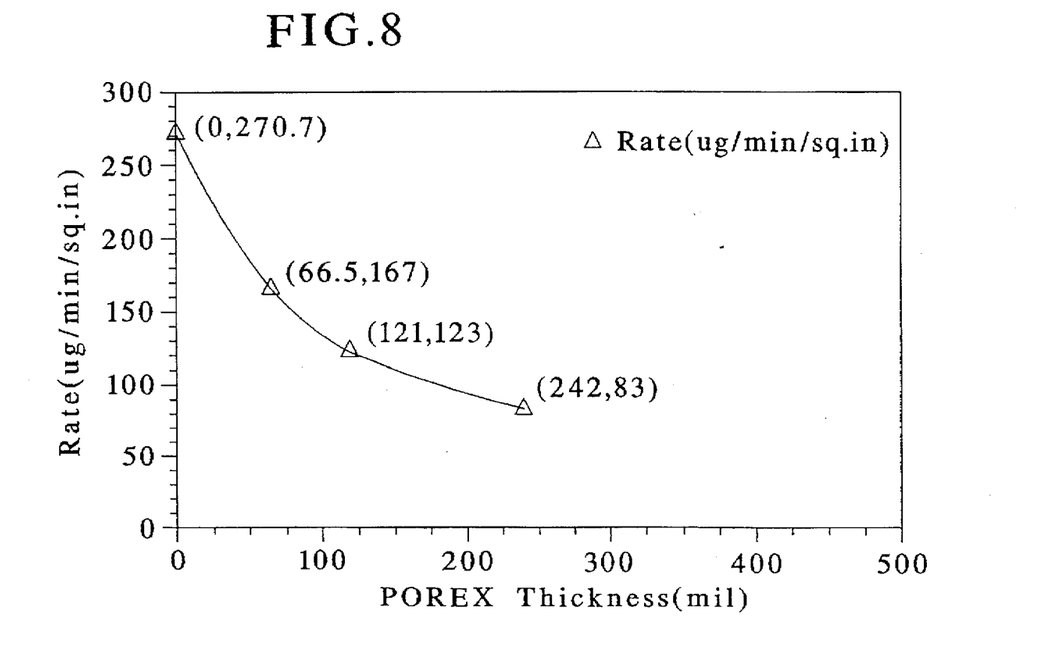
FIG. 8 also illustrates graphically results of Example No. 2 setting forth iodine release versus thickness of the material.

FIG. 7 illustrates the iodine release thickness contour plot for the extra fine microporous UHMWPE (5–15 μm). A constant release rate was observed for a given thickness. However, the iodine release rate is not a linear function of POREX thickness. Release rate approaches a plateau as the thickness passes 0.25", see FIG. 8.

Figure 9:
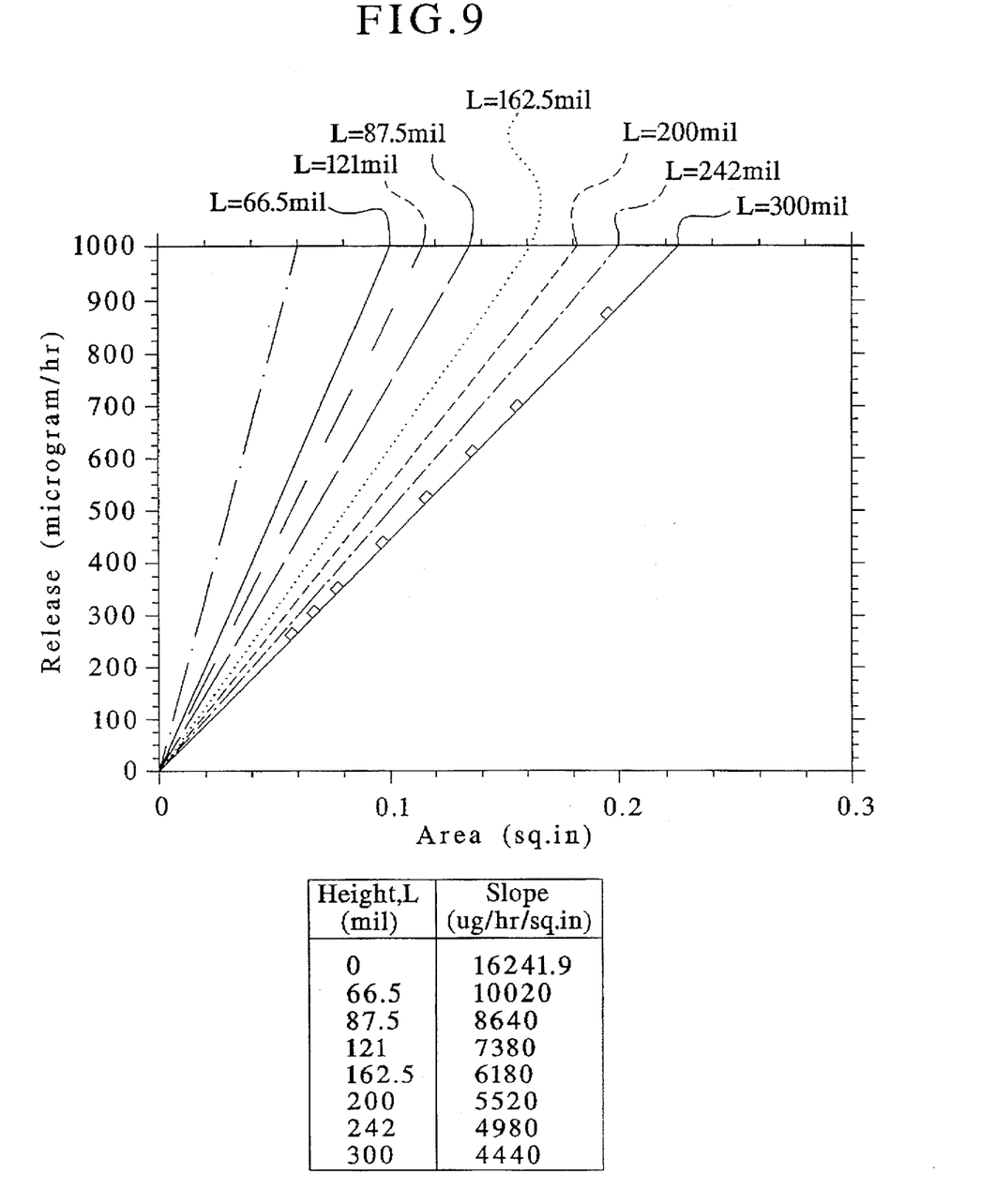
FIG. 9 illustrates graphically a model setting forth release rate versus rate-length cross-section area.

Based on this data, a model was then generated to assess and predict the iodine release rate per unit thickness of the microporous material and per unit release surface. FIG. 9 graphically illustrates this material. For instance, if one required 500 μg/hour of iodine release, a cross-section area of 0.1 in$^2$ in combination with a thickness of ~0.25" will be adequate. Iodine release rate could be increased by increasing the cross sectional area and decreasing the thickness.

EXAMPLE NO. 3

Release Plug Design and Characterization

Figure 10:
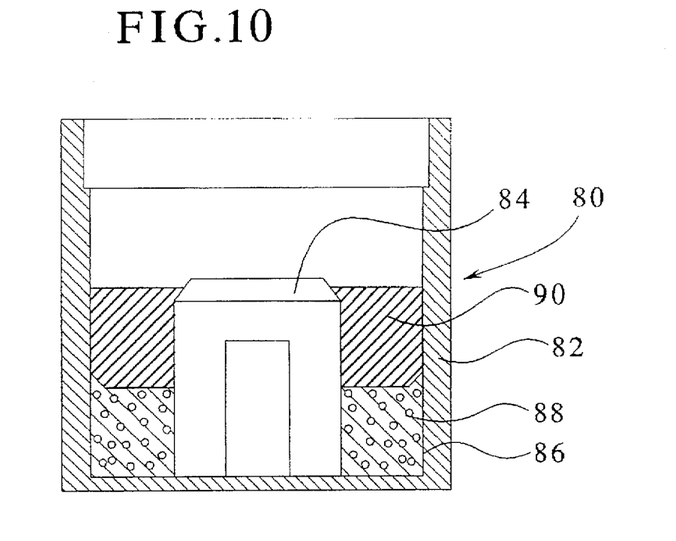
FIG. 10 illustrates schematically the device used in Example No. 3.

FIG. 10 illustrates schematically a device 80 to measure iodine release rate in a connector that is similar to the connector of the present invention. Wall members 82 define a cavity that includes a polysulfone member 84. The member 84 and wall member 82 define a chamber 86 that houses solid iodine 88. To tests the rate release, a UHMWPE POREX® plug 90 is placed over the iodine.

The release rate was measured in a continuous mode. Table No. 2, below, sets forth the release rate into various environments.

TABLE NO. 2

| Iodine Release Rate Into Various Environment | | |
|---|---|---|
| Release Into | Release Rate (μg/hour) | Measurement Method |
| Dianeal | 19.4# | Chemical analysis |
| Nutrineal | 175# | Chemical analysis |
| H$_2$O | 42 ± 7 | UV spectrophotometer |
| Open Air | 287 ± 24 | Gravimetric |
| Vacuum~20 in-Hg | 1500 | Gravimetric |
| Sublimation (in air) w/o plug | 1471 | Gravimetric |

*Except release to water, all other are constant rate.
Single point data determination.

Figure 11:
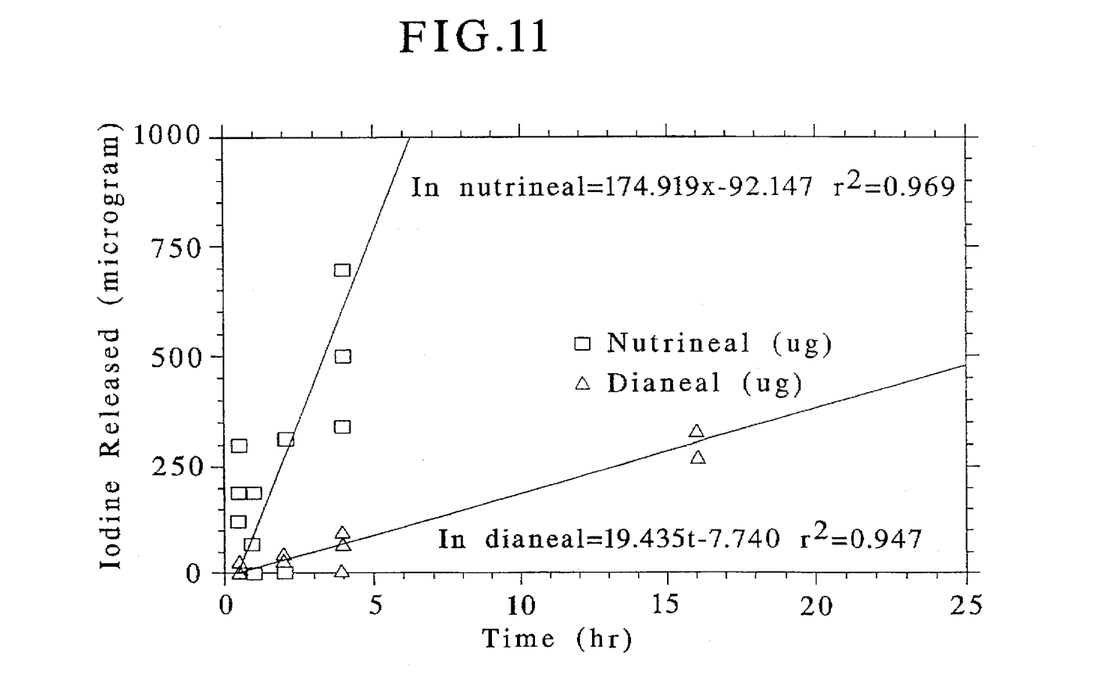
FIG. 11 illustrates graphically the results of Example No. 3 setting forth release rate over time.

FIG. 11 illustrates, graphically, the results of the experiment of Example No. 3. It should be noted that the iodine release rate into Nutrineal™ solution environment is about 9 to 10 times greater than in Dianeal® solution, see FIG. 11. This difference is favorable in the sense that the mechanism itself provides self regulation in iodine release base on demand. This also reduces toxicity levels and at the same time conserves iodine source.

It was noted that the iodine release rate in Dianeal® and Nutrineal™ is constant within the patient usage time frame. In other words, the release rate is not reduced as the concentration of the iodine in the solution increases or decreases. This particular design is able to provide an average of 174 μg/hr and 20 μg/hr in releasing to the Nutrineal™ and Dianeal® environment, respectively. Based on earlier estimations by one-time iodine loading (Table 1), roughly 200 ppm of iodine concentration is need to provide a 5 log kill. This means that the current design, at least in theory, should provide 5 log kill in one hour. Table 3 below sets forth the accuracy of the release rate production.

TABLE NO. 3

| Release to | lab. estimated ppm for 5 log kill | Actual device release rate | PPM conversion* |
|---|---|---|---|
| Dianeal | ~10 | 19 μg/hr | 19 ppm/hr |
| Nutrineal | ~200 | 174 μg/hr | 174 ppm/hr |

*PPM (μg/g) in the solution is depended on the amount of solution in the lumen of the connector. The less the volume, the higher the ppm. The conversion assumes 1 ml residual fluid.

Free iodine concentration for kill at a given time is probably less than the one time loaded situation. This required longer time to achieve 5 log kill for a continuous release system. However, the concentration can be increased by reducing the fluid volume, since ppm concentration at a given time is calculated as release rate divided by the fluid volume multiplied by the time. The lower the fluid volume, the higher the concentration.

Table Nos. 4 and 5 below illustrate the results in Nutrineal™ environment after the devices were exposed to Dianeal® and Nutrineal™ solutions continuously for one month. 1 cc of Dianeal® was used for soaking and was replaced three times a week.

TABLE NO. 4

| Properties | fluid cc | Device # #1 | #2 | #3 | #4 | #5 | #8 |
|---|---|---|---|---|---|---|---|
| log reduction | 1 CC | 0.5 | | 4 | | 2 | |
| Iodine measured (mg) | | 0.17 | 0.28 | 0.14 | 0.55 | 0.45 | — |
| release rate (μg/hr) | | 170 | 280 | 140 | 550 | 450 | — |
| log reduction | 0.5 CC | 3 | 3 | 5 | 5 | 5 | 5 |
| Iodine measured (mg) | | 0.33 | 0.24 | 0.38 | 0.3 | 0.38 | 0.28 |
| release rate (μg/hr) | | 165 | 120 | 190 | 150 | 190 | 140 |

TABLE NO. 5

| Fluid amount | Log reduction | total iodine (ppm) in 2 hours | iodine release rate |
|---|---|---|---|
| 1 cc | 2.2 ± 1.8 log | 310 ± 178 | 310* ± 178 μg/hr |
| 0.5 cc | 4.3 ± 1 log | 637 ± 112 | 159 ± 28 μg/hr |

*The cause of variation is unknown at this point.

The release rates are found comparable after one month of soaking in Dianeal® solution. They are 174 μg/hr and 159 μg/hr, respectively.

It appears that the average PPM (μg/g/2 hr) correlates better with the ~200 PPM requirement as established earlier for 5 log kill. The average PPM in 2 hours for the 0.5 CC Nutrineal solution is about 300. More PPM is needed in the controlled release simply due to the competing mechanism between the iodine complexization and the free iodine available for kill.

EXAMPLE NO. 5

Iodine Weight Determination for Transfer Set and Disinfect Connector

APD patient: 12 hours exchanges (8 p.m. to 8 a.m.) and 12 hours wet (8 a.m. to 8 p.m.). Iodine required for 6 months of service is calculated as [(287 μg/hr)×12 hr+(175 μg/hr)× 12 hr]×180 day=0.99792 gram ~=1 gram.

The first part of the calculation is based on open air release rate as the worst case. In the actual device, the loss is believed to be less. The second part of the calculation is based on Nutrineal solution environment. Again, this is worst case.

CAPD patient: 3 times Dianeal (12 hours), 1 time Nutrineal (worst case 8 hours overnight), total 4 hours exchanges maximum.

Iodine required for 6 months of service is calculated as 0.5 grams.

Lose in Dianeal=20 μg/hr×12 hr=240 μg

Lost in Nutrineal=175 μg/hr×8 hr=1400 μg

Lose in exchange=287 μg/hr×4 hr=1148 μg

Based on this preliminary calculation, 1 gram of iodine is needed.

SUMMARY

An iodine POREX design is able to provide ~170 μg/hr of iodine in the Nutrineal™ solution and ~20 μg/hr in the Dianeal® solution. To provide 5 log kill in 2 hours, 300 ppm on average (0–600 ppm in 2 hrs, in other words 600 ppm at the end of 2 hours control release) is needed for the Nutrineal™ solution and 10 PPM on average for the Dianeal® solution environment. Current POREX® dimension with 0.5 ml or less of residual fluid meets the average 5 log kill requirement. 1 gram of iodine is sufficient to provide 6 months of usage for both APD and CAPD patients and may be extended to one year of uses depending on the iodine consumption actually.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A device comprising:
   a body member;
   a chamber defined, at least in part, by a portion of the body member, the chamber including an interior having a solid sterilizing component that sublimes at ambient conditions to provide a sterilizing gas in the interior; and
   a controlled release member that defines, in part, the chamber and is so constructed and arranged to allow the sterilizing gas to pass in a rate controlled manner from the chamber through the controlled release member to the body member.

2. The device of claim 1 wherein the controlled release member is porous.

3. The device of claim 1 wherein the solid sterilizing component is iodine.

4. The device of claim 1 including means for coupling the device to another device.

5. The device of claim 1 including a fluid flow path through the device, the sterilizing gas contacting at least portions of the fluid flow path after it passes through the controlled release member.

6. The device of claim 1 including means for coupling the device to another device having a second fluid flow path and causing the fluid flow path and second fluid flow path to be in fluid communication.

7. A medical device comprising:
   a body member including a fluid flow pathway therethrough;
   a chamber member defining an interior, portions of the body member defining the chamber member, the chamber member including a controlled release member;
   a solid sterilizing compound located within the interior that sublimes at ambient conditions to provide a sterilizing gas in the interior; and the controlled release member being so constructed and arranged to allow at least some of the sterilizing gas to pass through the controlled release member and contact at least portions of the fluid flow pathway.

8. The device of claim 7 wherein the controlled release member is porous.

9. The device of claim 7 wherein the solid sterilizing component is iodine.

10. A system for coupling two flow pathways together comprising:

a first member including a first fluid flow pathway;

a second member including a second fluid flow pathway therethrough and a chamber member defining an interior, portions of the body defining the chamber, the chamber also being defined, in part, by a controlled release member, a solid sterilizing compound that sublimes at ambient conditions in the chamber providing a sterilizing gas in the interior, and the controlled release member is so constructed and arranged to allow at least some of the sterilizing gas to pass through the controlled release member and contact at least portions of the fluid flow pathway; and means for removably coupling the first and second members together so that the first and second fluid flow pathways are in fluid communication.

11. The system of claim 10 wherein the controlled release member is porous.

12. The system of claim 10 wherein the solid sterilizing compound is iodine.

13. A method for performing peritoneal dialysis comprising the steps of implanting in the patient a catheter that includes at an end thereof a device comprising:

a body member including a fluid flow pathway therethrough;

a chamber member defining an interior, the chamber being defined, in part, by a controlled release member;

a solid sterilizing compound located within the chamber that sublimes at ambient conditions to provide a sterilizing gas in the interior; and the controlled release member being so constructed and arranged to allow at least some of the sterilizing gas to pass through the controlled release member and contact at least portions of the fluid flow pathway.

14. The method of claim 13 wherein the solid sterilizing compound is a halogen.

* * * * *

UNITED STATES PATENT AND TRADEMARK OFFICE
CERTIFICATE OF CORRECTION

PATENT NO. : 5,733,270
DATED : March 31, 1998
INVENTOR(S) : Michael T.K. Ling, et al.

It is certified that error appears in the above-indentified patent and that said Letters Patent is hereby corrected as shown below:

Column 11, Line 15: directly beneath Table No. 4 please insert --The average log reduction and iodine release rate is seen in Table No. 5.--

Signed and Sealed this

Twenty-first Day of July, 1998

Attest:

BRUCE LEHMAN

*Attesting Officer*    *Commissioner of Patents and Trademarks*